United States Patent
Katchman et al.

(10) Patent No.: US 12,196,757 B2
(45) Date of Patent: Jan. 14, 2025

(54) AUTOANTIBODY BIOMARKERS FOR THE EARLY DETECTION OF OVARIAN CANCER

(71) Applicants: ARIZONA BOARD OF REGENTS ON BEHALF OF ARIZONA STATE UNIVERSITY, Scottsdale, AZ (US); THE BRIGHAM AND WOMEN'S HOSPITAL, INC., Boston, MA (US)

(72) Inventors: Benjamin Katchman, Tempe, AZ (US); Karen Anderson, Scottsdale, AZ (US); Garrick Wallstrom, Mesa, AZ (US); Joshua LaBaer, Chandler, AZ (US); Daniel Cramer, Chestnut Hill, MA (US)

(73) Assignees: ARIZONA BOARD OF REGENTS ON BEHALF OF ARIZONA STATE UNIVERSITY, Scottsdale, AZ (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 205 days.

(21) Appl. No.: 17/563,279

(22) Filed: Dec. 28, 2021

(65) Prior Publication Data

US 2022/0163531 A1 May 26, 2022

Related U.S. Application Data

(62) Division of application No. 16/317,184, filed as application No. PCT/US2017/041487 on Jul. 11, 2017, now Pat. No. 11,243,208.

(60) Provisional application No. 62/360,817, filed on Jul. 11, 2016.

(51) Int. Cl.
  *G01N 31/00* (2006.01)
  *G01N 33/53* (2006.01)
  *G01N 33/574* (2006.01)

(52) U.S. Cl.
  CPC ... *G01N 33/57449* (2013.01); *G01N 2800/60* (2013.01)

(58) Field of Classification Search
  None
  See application file for complete search history.

(56) References Cited

U.S. PATENT DOCUMENTS

| | | | |
|---|---|---|---|
| 4,444,879 | A | 4/1984 | Foster et al. |
| 9,857,374 | B2 | 1/2018 | LaBaer |
| 11,243,208 | B2* | 2/2022 | Katchman ........ G01N 33/57449 |
| 2014/0045915 | A1* | 2/2014 | Skog .................... C12Q 1/6806 435/15 |
| 2015/0362497 | A1 | 12/2015 | Anderson |
| 2016/0153053 | A1 | 6/2016 | Skog et al. |
| 2017/0045515 | A1 | 2/2017 | Anderson |
| 2017/0059563 | A1 | 3/2017 | Smith |
| 2017/0176423 | A1 | 6/2017 | Anderson |
| 2017/0363631 | A1 | 12/2017 | LaBaer |
| 2018/0067117 | A1 | 3/2018 | LaBaer |
| 2018/0172681 | A1 | 6/2018 | Katchman |
| 2018/0320230 | A1 | 11/2018 | LaBaer |

FOREIGN PATENT DOCUMENTS

| | | |
|---|---|---|
| AU | 2016202107 A1 | 4/2016 |
| WO | 2012021887 A2 | 2/2012 |
| WO | 2014120902 A1 | 8/2014 |
| WO | 2015148202 A1 | 10/2015 |
| WO | 2015148273 A2 | 10/2015 |
| WO | 2015167678 A1 | 11/2015 |
| WO | 2015168515 A1 | 11/2015 |
| WO | 2016094558 A1 | 6/2016 |
| WO | 2016195918 A1 | 12/2016 |
| WO | 2017075141 A1 | 5/2017 |
| WO | 2018013579 A1 | 1/2018 |
| WO | 2019099723 A2 | 5/2019 |

OTHER PUBLICATIONS

Gnjatic et al. (PNAS, Mar. 16, 2010, vol. 107, No. 11, pp. 5088-5093). (Year: 2010).*
Maggio (Immunoenzyme technique I, CRC press 1980, pp. 186-187). (Year: 1980).*
Kozak et al. (Biological Sciences, Oct. 1, 2003, 100(21) 12343-12348). (Year: 2003).*
Anderson et al. (Journal of Proteome, 2015, vol. 14, pp. 578-586). (Year: 2015).*
American Cancer Society. Cancer Facts & Figures 2015. Atlanta: American Cancer Society. 2015.
Anderson GL, et al. Assessing lead time of selected ovarian cancer biomarkers: a nested case-control study. J Natl Cancer Inst. 102:26-38.
Anderson KS, et al. Application of protein microarrays for multiplexed detection of antibodies to tumor antigens in breast cancer. Journal of proteome research. 2008;7:1490-9.
Anderson KS, et al. Autoantibody signature for the serologic detection of ovarian cancer. Journal of proteome research. 2015;14:578-86.
Anderson KS, et al. p53 autoantibodies as potential detection and prognostic biomarkers in serous ovarian cancer. Cancer Epidemiol Biomarkers Prev. 2010;19:859-68.
Anderson KS, et al. The sentinel within: exploiting the immune system for cancer biomarkers. Journal of proteome research. 2005;4:1123-33.
Anderson KS, et al. Using custom protein microarrays to identify autoantibody biomarkers for the early detection of breast cancer. San Antonio Breast Cancer Symposium. San Antonio, TX2008.
Anderson KS. Multiplexed detection of antibodies using programmable bead arrays. Methods in molecular biology. 2011;723:227-38.

(Continued)

*Primary Examiner* — Lisa V Cook
(74) *Attorney, Agent, or Firm* — Quarles & Brady, LLP (57) ABSTRACT

Compositions and methods relating to a panel of antigen biomarkers for the early detection of ovarian cancer. The compositions and methods encompass antigen biomarkers coupled to a substrate, with the biomarkers being selected from the group consisting of one or more of ICAM3, CTAG2, p53, STYXL1, PVR, POMC, NUDT11, TRIM39, UHMK1, KSR1, and NXF3.

7 Claims, 4 Drawing Sheets

(56) References Cited

OTHER PUBLICATIONS

Badgwell D, et al. Early detection of ovarian cancer. Dis Markers. 2007;23:397-410.
Bertenshaw GP, et al. Multianalyte profiling of serum antigens and autoimmune and infectious disease molecules to identify biomarkers dysregulated in epithelial ovarian cancer. Cancer Epidemiol Biomarkers Prev. 2008;17:2872-81.
Brown MC, et al. Oncolytic polio virotherapy of cancer. Cancer. 2014;120:3277-86.
Chapman C, et al. Autoantibodies in breast cancer: their use as an aid to early diagnosis. Ann Oncol. 2007;18:868-73.
Chatterjee M, et al. Diagnostic markers of ovarian cancer by high-throughput antigen cloning and detection on arrays. Cancer Res. 2006;66:1181-90.
Cramer DW, et al. Correlates of the preoperative level of CA125 at presentation of ovarian cancer. Gynecol Oncol. 2010;119:462-8.
Desmetz C, et al. Autoantibody signatures: progress and perspectives for early cancer detection. J Cell Mol Med. 2011;15:2013-24.
Grisanzio C, et al. Genetic and functional analyses implicate the NUDT11, HNF1B, and SLC22A3 genes in prostate cancer pathogenesis. Proceedings of the National Academy of Sciences of the United States of America. 2012;109:11252-7.
Hatakeyama S. Trim proteins and cancer. Nature reviews Cancer. 2011;11:792-804.
Henic E, et al. Cleaved forms of the urokinase plasminogen activator receptor in plasma have diagnostic potential and predict postoperative survival in patients with ovarian cancer. Clin Cancer Res. 2008;14:5785-93.
Jacobs IJ, et al. Ovarian cancer screening and mortality in the UK Collaborative Trial of Ovarian Cancer Screening (UKCTOCS): a randomised controlled trial. Lancet. 2016;387:945-56.
Kono T, et al. The CD155/poliovirus receptor enhances the proliferation of ras-mutated cells. International journal of cancer Journal international du cancer. 2008;122:317-24.
Koziol JA, et al. Recursive partitioning as an approach to selection of immune markers for tumor diagnosis. Clin Cancer Res. 2003;9:5120-6.
Lubin R, et al. Serum p53 antibodies as early markers of lung cancer. Nature medicine. 1995;1:701-2.
Moore RG, et al. A novel multiple marker bioassay utilizing HE4 and CA125 for the prediction of ovarian cancer in patients with a pelvic mass. Gynecol Oncol. 2009;112:40-6.
Murphy MA, et al. Epitope presentation is an important determinant of the utility of antigens identified from protein arrays in the development of autoantibody diagnostic assays. Journal of proteomics. 2012;75:4668-75.

Nakabeppu Y. Cellular levels of 8-oxoguanine in either DNA or the nucleotide pool play pivotal roles in carcinogenesis and survival of cancer cells. International journal of molecular sciences. 2014; 15:12543-57.
Palmer C, et al. Systematic evaluation of candidate blood markers for detecting ovarian cancer. PLoS One. 2008;3:e2633.
Pedersen JW, et al. Early detection of cancer in the general population: a blinded case-control study of p53 autoantibodies in colorectal cancer. British journal of cancer. 2013;108:107-14.
Ramachandran N, et al. Next-generation high-density self-assembling functional protein arrays. Nature methods. 2008;5:535-8.
Reuschenbach M, et al. A systematic review of humoral immune responses against tumor antigens. Cancer immunology, immunotherapy : CII. 2009;58:1535-44.
Shi JX, et al. Tumor associated antigens or anti-TAA autoantibodies as biomarkers in the diagnosis of ovarian cancer: a systematic review with meta-analysis. Expert review of molecular diagnostics. 2015;15:829-52.
Simon I, et al. Evaluation of the novel serum markers B7-H4, Spondin 2, and DcR3 for diagnosis and early detection of ovarian cancer. Gynecol Oncol. 2007;106:112-8.
Vitonis AF, et al. Assessing ovarian cancer risk when considering elective oophorectomy at the time of hysterectomy. Obstet Gynecol. 2011;117:1042-50.
Wang J, et al. A versatile protein microarray platform enabling antibody profiling against denatured proteins. Proteomics Clin Appl. 2013;7:378-83.
Wang J, et al. Plasma Autoantibodies Associated with Basal-like Breast Cancers. Cancer Epidemiol Biomarkers Prev. 2015;24:1332-40.
Wang X, et al. Autoantibody signatures in prostate cancer. N Engl J Med. 2005;353:1224-35.
Wong J, et al. Rapid detection of antibodies in sera using multiplexed self-assembling bead arrays. Journal of immunological methods. 2009;350:171-82.
Yousef GM, et al. The human kallikrein gene family: new biomarkers for ovarian cancer. Cancer Treat Res. 2009;149:165-87.
Zhang L, et al. TRIM39 regulates cell cycle progression and DNA damage responses via stabilizing p21. Proceedings of the National Academy of Sciences of the United States of America. 2012;109:20937-42.
Zhang Z, et al. Combining multiple serum tumor markers improves detection of stage I epithelial ovarian cancer. Gynecol Oncol. 2007;107:526-31.
Maggio (Immunoenzyme technique I, CRC press copyright 1980, pp. 186-187). (Year: 1980).
Katchman, B. A., et al., "Proteomic mapping of p53 immunogenicity in pancreatic, ovarian, and breast cancers," Proteomics—Clinical Applications, Jul. 1, 2016, vol. 10, No. 7, pp. 720-731.
International Search Report and Written Opinion issued Oct. 3, 2017, in related International Application No. PCT/US2017/041487, 11 pages.

\* cited by examiner

AUTOANTIBODY BIOMARKERS FOR THE EARLY DETECTION OF OVARIAN CANCER

CROSS-REFERENCE TO RELATED APPLICATION

This application is a divisional of U.S. patent application Ser. No. 16/317,184, filed Jan. 11, 2019, now U.S. Pat. No. 11,243,208, which claims priority to U.S. Provisional Patent Application No. 62/360,817 filed on Jul. 11, 2016, the disclosure of each of which are incorporated herein by reference.

STATEMENT REGARDING FEDERALLY SPONSORED RESEARCH

The invention was made with government support under U01 CA117374 awarded by the National Institutes of Health. The government has certain rights in the invention.

FIELD OF THE INVENTION

This disclosure is related to biomarkers and methods for the early identification of ovarian cancer.

BACKGROUND OF THE INVENTION

Ovarian cancer remains a leading cause of death from gynecologic malignancy, with over 21,290 new cases/year and an estimated 14,180 deaths in the United States in 2014. The 5-year survival rate for stage I ovarian cancer is over 80%, compared with a survival rate of only 11% for stage IV ovarian cancer. Early diagnosis is also associated with improved morbidity. Unfortunately, over 60% of patients have advanced disease at the time of diagnosis.

This is likely related to several factors, including tumor biology that causes rapid, early dissemination through the peritoneum, as well as limitations of current biomarkers and imaging modalities for early detection. A number of screening strategies and biomarkers have been proposed to improve the early detection of ovarian cancer. Two biomarkers cancer antigen 125 (CA 125) and human epididymis protein 4 (HE4) as well as two algorithms, OVA1 and Risk of Ovarian Malignancy Algorithm (ROMA), have been approved by the US FDA for risk assessment and management of ovarian cancer. The most common approaches used in screening are sequential testing using serum CA 125 and transvaginal ultrasound (TVUS) have been shown to have a high specificity (99.9%) and positive predictive value (PPV; 26.8%).

Overall, these strategies are limited by the low prevalence of the disease in the general population, interpatient variability of CA 125 testing, false positive CA 125 levels from benign ovarian tumors and diverticulitis, as well as the limited specificity of pelvic ultrasound for detection of early ovarian cancers. Moreover, there are currently no screening biomarkers recommended for use in the general population. Thus, there is an urgent need to identify biomarkers and to complement CA 125 and HE4 for the early identification of ovarian cancer.

SUMMARY OF THE INVENTION

In certain embodiments, a panel of novel serum tumor antigen-associated autoantibodies (TAAb) biomarkers for the early diagnosis of serous ovarian cancer is disclosed.

In other embodiments, detection, diagnostic, and treatment-related methods are disclosed. Sera from patients with ovarian cancer contain tumor antigen-associated autoantibodies (TAAb) to tumor-derived proteins. For example, to detect TAAb, high-density programmable protein microarrays (NAPPA) expressing 10,247 candidate tumor antigens were probed with sera from patients with serous ovarian cancer and bound IgG measured. A set of 735 antigens was selected and probed with an independent set of serous ovarian cancer sera. Eleven potential autoantigens were identified with sensitivities ranging from 3-39.7% at >93% specificity as well as a combined sensitivity of 45% at 100% specificity.

These and other aspects will be apparent upon reference to the following detailed description and figures. To that end, any patent and other documents cited herein are hereby incorporated by reference in their entirety.

BRIEF DESCRIPTION OF THE DRAWINGS

FIG. 2A-C. Quality control of protein microarrays. A. Quality control of DNA printing with picogreen. B. Quality control of in vitro protein production with anti-GST Mab staining. C. Reproducibility of protein signal intensity of two protein arrays produced in a single print batch.

FIG. 3A-B. Autoantibody responses in serous ovarian cancer A. training set and B. validation set. P-value was calculated by a two-tail t test and * indicates statistically significant antigens (p<0.05). Data is presented as antibody Relative Light Unit (RLU) ratio (Antigen: GST control ratio).

FIG. 4A-B. ROC classifier of the A. 11 TAAb classifier (CTAG2, ICAM3, KSR1, NUDT11, NXF3, POMC, PVR, STYXL1, TP53, TRIM39, and UHMK1) and B. p53 and CTAG2 classifier was calculated using a binary logistic regression analysis. The dotted line indicates the training set, consisting of serous ovarian cases, n=29 vs benign disease and healthy controls, n=58) and the solid line indicates the validation set (serous ovarian cases, n=34 vs healthy controls, n=32). We used the values obtained from our validation set to report our sensitivity and specificity.

DETAILED DESCRIPTION OF THE INVENTION

Embodiments described herein relate to methods for identifying autoantibodies as potential biomarkers for the early detection of ovarian cancer, as well as to kits for utilizing said autoantibodies as diagnostic biomarkers and for personalized medicine/therapeutics assessment and treatment.

The technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

In cancer, tumor antigen-associated autoantibodies (TAAb) represents a source of potential early diagnostic biomarkers for ovarian cancer. TAAbs are generated in response to protein overexpression or mutations in cancer patients. Research has identified panels of TAAbs for the detection of breast, prostate, colorectal, lung, and ovarian cancers. In addition to CA 125 and HE4, serum antibodies to p53 are the most frequently studied TAAb in ovarian cancer. Mutations in TP53 occur early in ovarian carcinogenesis, are present in over 80% of serous ovarian cancer, and are strongly associated with the presence of p53-TAAb.

As used herein, "sensitivity" is the probability that the biomarker is positive for patients who benefit from T (an experimental control) relative to C (a control) within a randomized clinical trial. "Specificity" is the probability that the biomarker is negative for patients who do not benefit from T relative to C.

A therapeutically effective dose relates to the amount of a compound which is sufficient to improve the symptoms, for example a treatment, healing, prevention or improvement of such conditions. An "effective amount" of the pharmaceutical composition is defined herein as that amount sufficient to induce oncolysis, the disruption or lysis of a cancer cell, as well as slowing, inhibition or reduction in the growth or size of a tumor and includes the eradication of the tumor in certain instances.

In view of the disclosure herein, it will be appreciated that certain embodiments relate to a composition, and, for example, a diagnostic kit, including a panel of antigen biomarkers for the early detection of ovarian cancer coupled to a substrate by any means known in the art, wherein the biomarkers are selected from the group consisting of one or more of: ICAM3, CTAG2, p53, STYXL1, PVR, POMC, NUDT11, TRIM39, UHMK1, KSR1, and NXF3. The composition can further include a complex formed by an antibody and an antigen in vitro, for example, a STYXL1-Ab complex where the Ab is from a patient sample.

Moreover, methods for detecting ovarian cancer onset are disclosed that include contacting a fluid from a patient that contains immunoglobulins with a substrate having one or more biomarkers selected from the group consisting of ICAM3, CTAG2, p53, STYXL1, PVR, POMC, NUDT11, TRIM39, UHMK1, KSR1, and NXF3.; and detecting whether one or more of the biomarkers is bound by the immunoglobulins. Preferably, the substrate and one or more biomarkers comprises a Nucleic Acid Protein Programmable Array (NAPPA).

In certain embodiments, treatment following early stage detection methods are disclosed. For example, a method for selectively administering a therapeutically effective treatment following early stage ovarian cancer detection in a patient includes contacting a fluid that contains immunoglobulins from a patient with a substrate having one or more biomarkers selected from the group consisting of ICAM3, CTAG2, p53, STYXL1, PVR, POMC, NUDT11, TRIM39, UHMK1, KSR1, and NXF3; detecting whether one, preferably two, or more of the aforesaid biomarkers is bound by the patient's immunoglobulins, and then selectively administering a therapeutically effective treatment for a patient.

As shown in Table 2, there has been established a cutoff value for each antigen. Generally, for confidence a patient should express two or more of the antigens (which would generate the antibodies detected by a method disclosed herein) used in the panel to be considered positive. If two or more antigen biomarkers are detected, further diagnostic and therapeutic intervention would be recommended. For example, the diagnostic procedure may be a biopsy, and the therapeutic intervention may be a treatment selected from the group consisting of a surgical intervention, a chemotherapeutic intervention, and a radiotherapeutic intervention.

EXAMPLES

Methods
Patient Sera

Sera from patients with serous ovarian cancer were obtained from the Brigham and Women's Hospital. Sera derived from ovarian cancer patients were obtained at the time of presentation prior to surgery. Sera from age-, gender-, and location-matched general population control women were obtained using a standardized serum collection protocol and stored at −80° C. until use. Cases and matched controls were processed simultaneously. Women with a personal history of cancer (other than non-melanoma skin cancer) were excluded as controls (Table 1). These sera have been reported in. Written consent was obtained from all subjects under institutional review board approval.

TABLE 1

Characteristics of cases and controls.
Characteristics of Cases and Controls

| | | Discovery Set | | | Training Set | | | | Validation Set | | |
|---|---|---|---|---|---|---|---|---|---|---|---|
| | | Controls (N = 30) N (%) | Serous Cases (N = 30) N (%) | Chi-square p-value* | Controls (N = 30) N (%) | Benign controls (N = 30) N (%) | Serous Cases (N = 30) N (%) | Chi-square p-value* | Controls (N = 32) N (%) | Serous Cases (N = 34) N (%) | Chi-square p-value* |
| Age | | | | | | | | | | | |
| | <50 | 6 (20.0%) | 6 (20.0%) | 0.99 | 12 (40.0%) | 12 (40.0%) | 11 (36.7%) | 0.99 | 1 (3.1%) | 2 (5.9%) | 0.85 |
| | 50-60 | 12 (40.0%) | 12 (40.0%) | | 11 (36.7%) | 11 (36.7%) | 11 (36.7%) | | 10 (31.2%) | 11 (32.4%) | |
| | >60 | 12 (40.0%) | 12 (40.0%) | | 7 (23.3%) | 7 (23.3%) | 8 (26.7%) | | 21 (65.6%) | 21 (61.8%) | |

TABLE 1-continued

Characteristics of cases and controls.
Characteristics of Cases and Controls

| | Discovery Set | | | Training Set | | | | Validation Set | | |
|---|---|---|---|---|---|---|---|---|---|---|
| | Controls (N = 30) N (%) | Serous Cases (N = 30) N (%) | Chi-square p-value* | Controls (N = 30) N (%) | Benign controls (N = 30) N (%) | Serous Cases (N = 30) N (%) | Chi-square p-value* | Controls (N = 32) N (%) | Serous Cases (N = 34) N (%) | Chi-square p-value* |
| Menopausal status | | | | | | | | | | |
| Pre | 8 (26.7%) | 6 (20.0%) | 0.54 | 13 (43.3%) | 10 (33.3%) | 10 (33.3%) | 0.65 | 3 (9.4%) | 3 (8.8%) | 0.94 |
| Post | 22 (73.3%) | 24 (80.0%) | | 17 (56.7%) | 20 (66.7%) | 20 (66.7%) | | 29 (90.6%) | 31 (91.2%) | |
| Race | | | | | | | | | | |
| White | 30 (100.0%) | 30 (100.0%) | — | 30 (100.0%) | 27 (90.0%) | 23 (88.5%) | 0.17 | 30 (93.8%) | 32 (97.0%) | 0.54 |
| Non-white | 0 (0%) | 0 (0%) | | 0 (0%) | 3 (10.0%) | 3 (11.5%) | | 2 (6.2%) | 1 (3.0%) | |
| DC use | | | | | | | | | | |
| Ever | 10 (33.3%) | 13 (43.3%) | 0.43 | 10 (33.3%) | 11 (36.7%) | 10 (38.5%) | 0.92 | 18 (56.2%) | 20 (60.6%) | 0.72 |
| Never | 20 (66.7%) | 17 (56.7%) | | 20 (66.7%) | 19 (63.3%) | 16 (61.5%) | | 14 (43.8%) | 13 (39.4%) | |
| Parity | | | | | | | | | | |
| Nulliparous | 4 (13.3%) | 6 (20.7%) | 0.45 | 5 (16.7%) | 9 (30.0%) | 7 (26.9%) | 0.46 | 3 (9.4%) | 3 (8.8%) | 0.94 |
| Parous | 26 (86.7%) | 23 (79.3%) | | 25 (83.3%) | 21 (70.0%) | 19 (73.1%) | | 29 (90.6%) | 31 (91.2%) | |
| Year of specimen collection | | | | | | | | | | |
| 2001-2002 | 10 (33.3%) | 8 (26.7%) | 0.4 | 8 (26.7%) | 10 (33.3%) | 3 (10.0%) | 0.19 | 10 (31.2%) | 11 (32.4%) | 0.91 |
| 2003-2005 | 8 (26.7%) | 13 (43.3%) | | 13 (43.3%) | 11 (36.7%) | 12 (40.0%) | | 15 (46.9%) | 17 (50.0%) | |
| 2006-2010 | 12 (40.0%) | 9 (30.0%) | | 9 (30.0%) | 9 (30.0%) | 15 (50.0%) | | 7 (21.9%) | 6 (17.6%) | |
| Length of storage | | | | | | | | | | |
| <5.4 years | 13 (43.3%) | 9 (30.0%) | 0.07 | 11 (36.7%) | 10 (33.3%) | 17 (56.7%) | 0.25 | 3 (25.0%) | 8 (23.5%) | 0.84 |
| 5.44-7.6 years | 84 (13.3%) | 12 (40.0%) | | 9 (30.0%) | 10 (33.3%) | 9 (30.0%) | | 11 (34.4%) | 14 (41.2%) | |
| >7.6 years | 13 (43.3%) | 9 (30.0%) | | 10 (33.3%) | 10 (33.3%) | 4 (13.3%) | | 13 (40.6%) | 12 (35.3%) | |

Sample Characteristics and Biomarker Selection

The primary goal of this study was to identify serum TAAb biomarkers that would distinguish serous ovarian cancer from both benign disease and healthy controls in order to improve the sensitivity of current biomarkers and guide clinical decisions. We performed a sequential screening strategy, described in FIG. 1, in order to identify a panel of TAAb biomarkers from 10,247 full-length human proteins. All the discovery and validation case and control sera were gender- and age-matched. Sera from cases, primarily stage III/IV (95%), grade 3 (93.7%), was collected prior to surgery under standard collection protocols [16]. Table I details the age distribution, menopausal status, race, oral contraceptive (OC) use, parity, grade, year of sample collection, and length of storage.

Protein Microarray Production

Figure 2A:
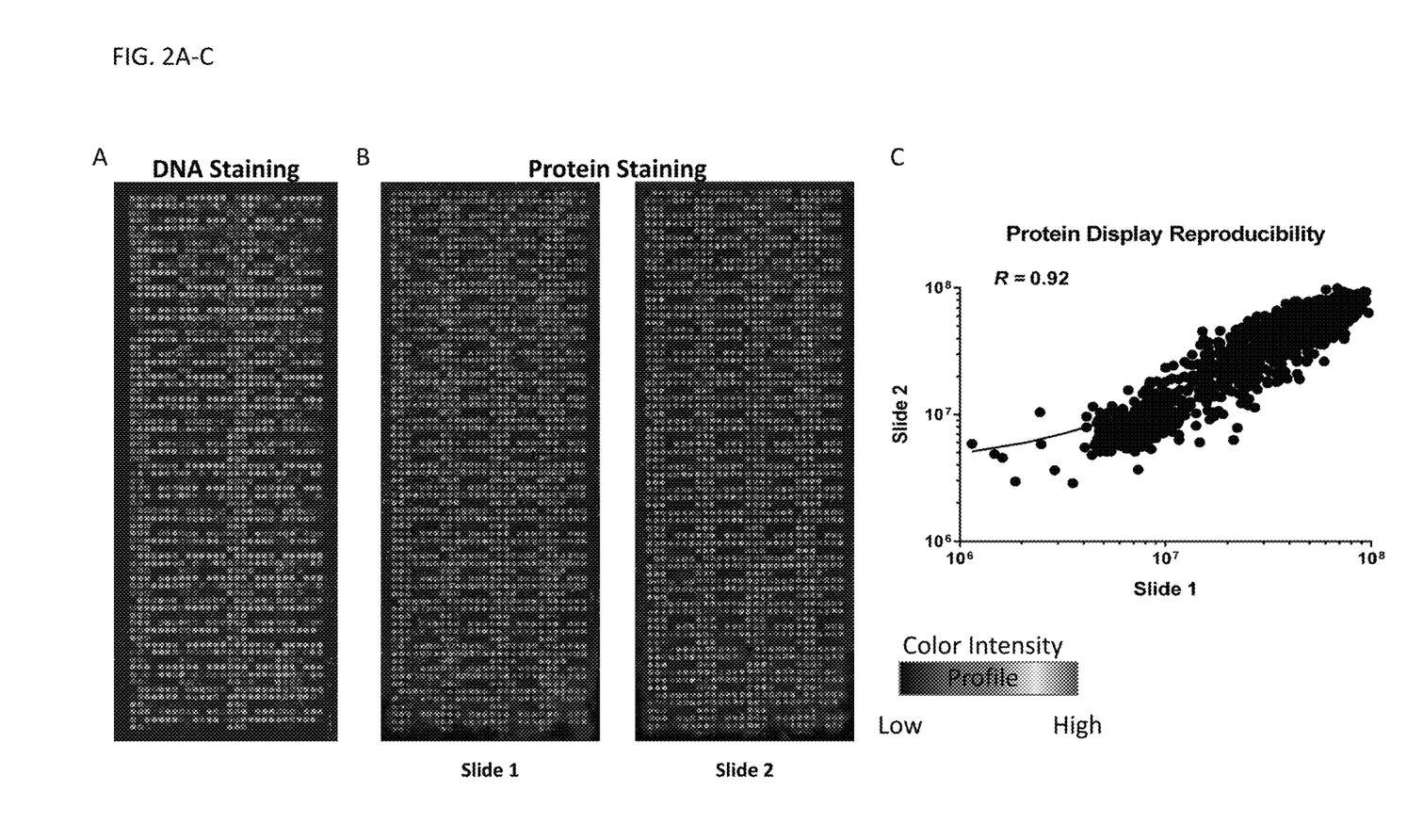

Sequence-verified, full-length cDNA expression plasmids in the T7-based mammalian expression vector pANT7_cGST were obtained from Arizona State University's Biodesign Institute Plasmid Repository and are publicly available through DNASU (http://dnasu.asu.edu/DNASU/). The high-throughput preparation of high-quality supercoiled DNA for cell-free protein expression was performed as described [21]. Protein arrays displaying 10,247 human proteins were distributed evenly over five slides. Quality control was performed to determine inter and intra assay consistency by measuring DNA and protein expression (FIG. 2).

Protein Array Screening Protocol

The slides were initially blocked with 1× Superblock® (Pierce, MA, USA) for 1 hour at 30° C. In vitro transcription translation (IVTT) was performed using HeLa lysate, Accessory Proteins, and Reaction Mix from Thermo Scientific (Carlsbad, CA, USA). Per the manufacturer's recommendations, Hela Lysate was slowly injected onto the slide and the expression of the proteins was automated in two steps: 1. Hybridization at 30° C. for 90 minutes with no agitation; 2. Hybridization at 15° C. for 30 minutes with no agitation using an EchoTherm Chilling Incubator (Torrey Pines Scientific, Inc. Carlsbad, CA, USA). Following the IVTT step the slides are washed with 0.2% PBST then with 5% milk in 0.2% PBST [21].

Image Analysis and Quantification

Image analysis and quantification were performed as previously described [11]. Briefly, slides were scanned using a PowerScanner™ (Tecan, Mannedorf, Switzerland) and the spot intensity was measured using ArrayPro Analyzer (MediaCybernetics, Rockville, MD, USA). Raw intensity values were normalized by the following steps: 1. Remove background by subtracting non-spot control using the first quartile value (Background); 2. Determine the median intensity of every gene, excluding the control spots (Median Protein Intensity); 3. Subtract the raw signal intensity from the background and divide it over the median protein intensity minus the background. In addition, the visual intensity of captured antibodies was evaluated by at least two researchers to identify and confirm positive responses, previously described in [24]. Visually, antigens were selected for further validation if a ring was present in two or more cases and not identified in controls.

Antigen Selection Criteria for Validation Protein Arrays

Using the normalized values from the discovery array, for each protein antigen we determined the sensitivity at 95% and 98% specificity, area under receiver operating characteristics curve (AUC), partial AUC above 95% and 98% specificity (pAUC), including the Welch's t test P value. We also used the K-statistic as previously described in [11]. Briefly, the K-statistic measures the separation of the top 20 percentile of antigens by evaluating qcases(0.975)–qcases (0.800) divided by qcontrols(0.975)–qcontrols(0.025). A higher K value indicates a greater separation of the antibody reactivity of positive cases and negative controls. Antibodies with the same sensitivity as other markers but a higher K-statistic were selected for further validation.

Custom validation NAPPA arrays were composed of antigens that met at least one of the following criteria: (a) ≥10% sensitivity at 95% specificity, (b) ≥0.500 AUC, (c) ≥0.700 pAUC, (d) significant P value of Welch t test, (e) K≥0.9, and (f) antigens with a greater prevalence in cases than in controls by visual analysis. In total, 735 full-length proteins were included for further validation (Supplemental Table 2). These antigens were manufactured as described above and printed in duplicate on a single microarray. The protein array data discussed in this manuscript have been deposited in the National Center for Biotechnology Information's Gene Expression Omnibus (GEO) and are accessible through GEO Super Series accession number GSE79517.

Rapid ELISA

Rapid Antigenic Protein In situ Display (RAPID) ELISA was performed as previously described [25], with the following modifications. All GST fusion proteins were expressed from plasmids using 1-Step Human Coupled in vitro Expression system (Thermo Scientific) at 30° C. for 1.5 hours. Following in vitro protein expression, the GST-fused proteins were diluted 1:100 in 5% milk in 0.2% PBST and added to the GST coated 96 well plates at 100 µl/well and shaken at room temperature at 500 rpm for 1 hour. Plates were then washed 5 times with 0.2% PBST. During incubation the patient serum was diluted 1:500 in 50% E. coli lysate and 5% Milk in 0.2% PBST. Plates were then incubated with 100 µl/well diluted patient serum, with shaking at RT at 500 rpm for 1 hour, and washed 5 times with 0.2% PBST. Secondary HRP conjugated goat anti-human IgG (Jackson ImmunoResearch Laboratories) to detect serum TAAb were diluted 1:10,000 in 5% milk in 0.2% PBST, and the GST positive control secondary HRP sheep anti-Mouse IgG (Jackson ImmunoResearch Laboratories) was diluted 1:6250. The secondary Abs were shaken at RT at 500 rpm for 1 hour. Plates were washed 5 times in 0.2% PBST prior to the addition of the developing buffer, Supersignal ELISA Femto Chemiluminescent Substrate (Thermo Scientific). Relative luminescence units (RLU) were measured on a Glomax 96 Microplate Luminometer (Promega, Madison, WI) using a wavelength of 425 nm. All assays were performed in duplicate, and values are plotted as mean values. RLU ratios were calculated using the RLU of a specific antigen divided by the RLU of the control GST-protein. The sensitivity and specificities of TAAb levels was determined by applying a cutoff value of the mean of the controls plus two standard deviations. We performed a two-tailed t-test to determine significance.

Statistical Analysis

ROC analysis was performed utilizing normalized values from our orthogonal RAPID ELISA assay without feature selection, using a binary logistic regression analysis. We selected an 11-TAAb panel (ICAM3, CTAG2, p53, STYXL1, PVR, POMC, NUDT11, TRIM39, UHMK1, KSR1, and NXF3) to develop a classifier based on their individual sensitivity and specificity. The binary logistic regression analysis classifier was trained on normalized RAPID ELISA values from Training Set and tested on normalized RAPID ELISA values from Validation Set. Samples were selected as positive if they exceed antigen specific cutoffs of two standard deviations the mean of the benign ovarian disease controls. Antigen specific cutoffs were set to achieve 95% specificity by only selecting antigens for the classifier if they met ≥10% sensitivity at ≥95% specificity (Table 2).

TABLE 2

| | Training Set-RAPID ELISA (Serous Ovarian Cancer, n = 29; Benign Disease Control, n = 30; Healthy Control, n = 28) | | | | | | Validation Set-RAPID ELISA (Serous Ovarian Cancer, n = 34; Healthy Control, n = 32) | | |
|---|---|---|---|---|---|---|---|---|---|
| | Benign vs Cases | | | Healthy vs Cases | | | Healthy vs Cases | | |
| Antigen | Sensitivity | Specificity | Cutoffs (25 D) | Sensitivity | Specificity | Cutoffs (25 D) | Sensitivity | Specificity | Cutoffs (25 D) |
| CTAG2 | 0.103 | 0.967 | 2.088 | 0.103 | 0.967 | 1.882 | 0.235 | 0.968 | 3.465 |
| ICAM3 | 0.034 | 1.000 | 1.711 | 0.034 | 1.000 | 1.900 | 0.176 | 0.968 | 1.801 |
| KSR1 | 0.137 | 0.933 | 2.605 | 0.000 | 0.933 | 3.224 | 11.8 | 0.968 | 2.001 |
| NUDT11 | 0.275 | 0.967 | 2.436 | 0.275 | 0.967 | 2.734 | 0.324 | 1.000 | 2.345 |
| NXF3 | 0.034 | 0.900 | 2.085 | 0.034 | 0.900 | 1.473 | 0.088 | 0.968 | 3.686 |
| POMC | 0.068 | 0.933 | 2.250 | 0.172 | 0.933 | 1.649 | 0.118 | 0.937 | 2.804 |
| PVR | 0.137 | 0.933 | 1.468 | 0.207 | 0.933 | 1.366 | 0.176 | 0.968 | 2.734 |
| STYLX1 | 0.138 | 0.933 | 1.813 | 0.275 | 0.933 | 1.583 | 0.088 | 0.968 | 4.878 |
| TP53 | 0.069 | 0.967 | 3.171 | 0.067 | 0.967 | 2.310 | 0.441 | 0.968 | 6.012 |
| TRIM39 | 0.241 | 0.967 | 2.477 | 0.034 | 0.967 | 19.130 | 0.147 | 0.968 | 6.912 |
| UHMK1 | 0.034 | 0.900 | 2.006 | 0.138 | 0.900 | 1.539 | 0.118 | 0.968 | 2.387 |
| Combined Sensitivity | >2 antigens = 11/29 = 37.9% | | | >2 antigens = 9/29 = 31% | | | >2 antigens = 16/34 = 47.1% | | |
| Combined Specificity | >2 antigens = 2/30 = 93.3% | | | >2 antigens = 2/28 = 92.8% | | | >2 antigens = 2/32 = 93.7% | | |

Results

Figure 1:
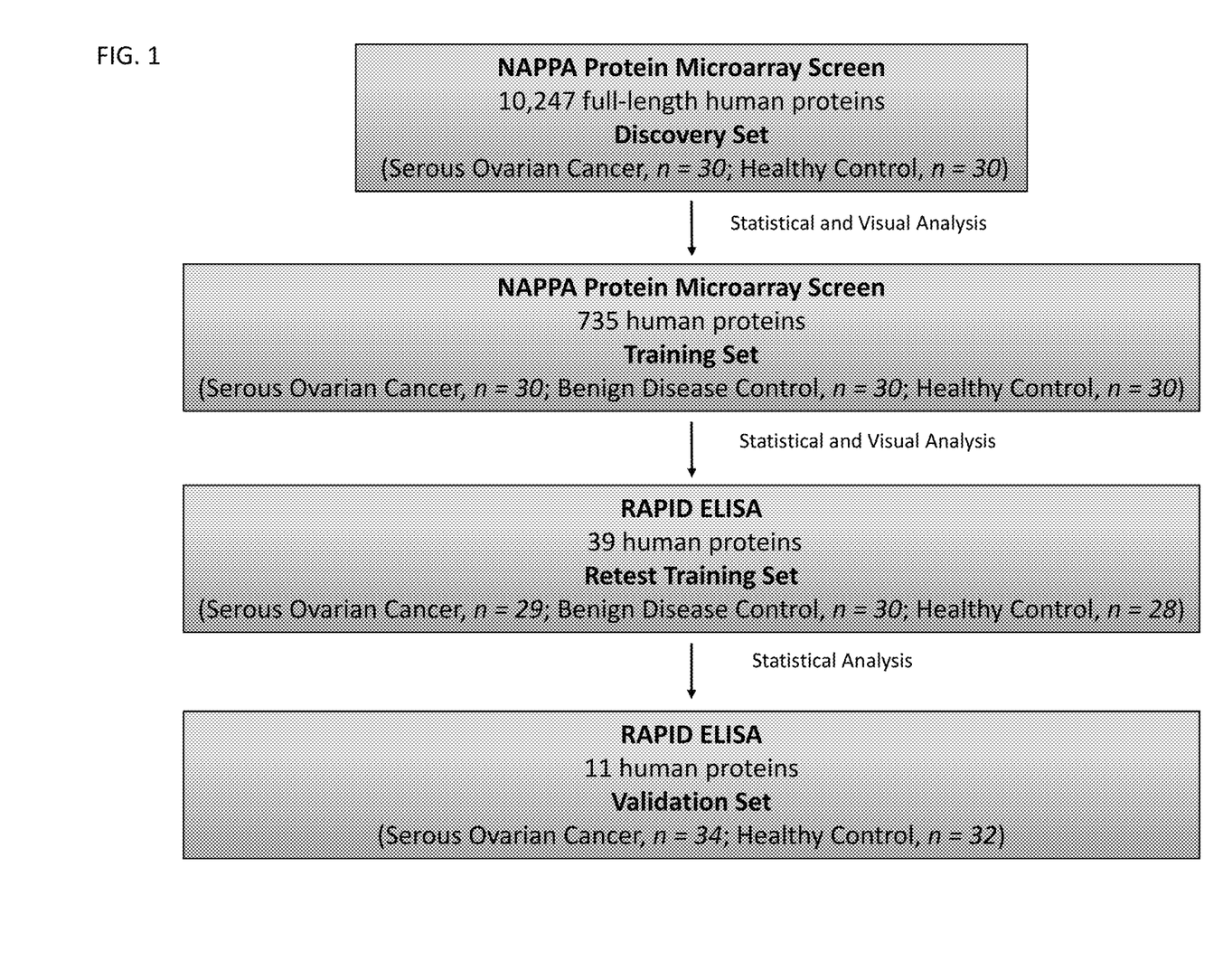
FIG. 1. Overview of study design.

Tumor Antigen-Associated Autoantibody Screen of 10,247 Human Antigens Using NAPPA Protein Microarrays In the discovery phase, we performed a comprehensive analysis of 10,247 full-length human proteins against 30 patients with serous ovarian cancer and 30 healthy controls to identify potential serum IgG TAAb biomarkers associated with serous ovarian cancer (FIG. 1). The entire cohort consisted of 94 women with newly diagnosed serous ovarian cancer, 92 healthy control women, and 30 women with benign ovarian disease (Table 1), including 19 patients with serous cystadenomas and 11 patients with mucinous cystadenomas. For each set, cases were intentionally matched to controls for age and gender. The median age at diagnosis was 60 years of age and were >85% white. Because the training set included women with benign ovarian disease, all cases and controls in that set were younger, on average, than the other sets (median age 54 vs 62.5). As seen in Table 1, cases and controls were balanced for menopausal status, oral contraceptive use, parity, and year of sample collection. The discovery set cases were stored longer than controls (p=0.07) but this variable was evenly distributed for the remaining datasets.

The goal of the discovery screen was to eliminate uninformative antigens as well as reducing the false positive rate and lower the overall cost of the screen. Sample protein arrays are shown in FIG. 2. The batch-to-batch variation of DNA printing was R=0.97 and protein expression, as measured by anti-GST monoclonal antibody binding, was R=0.92 (FIG. 2). The interassay reproducibility of serum screening is shown in FIG. 2C, and was R=0.92. In order to identify candidate TAAbs among the 10,247 antigens that distinguish serous ovarian cancer from healthy controls, we selected antigens based on statistical significance and visual analysis (see Methods).

Selection of Antigens for Training of Biomarker Panel

We selected 735 antigens for training and printed each antigen in duplicate for testing with sera form the Training Set. These arrays consisted of 649 antigens with sensitivities above 10% at 95% specificity and/or K>0.9 in our Discovery Set. Visually, we also selected 86 antigens to be included in our focused 735 antigen array. The selected 735 antigens were screened with the separate sera Training Set consisting of 30 cases of serous ovarian cancer, 30 benign disease controls, and 30 matched healthy controls (Supplementary Table 2). The inclusion of sera from women with benign ovarian disease at this early stage of biomarker discovery is critical to limit false positive detection and for ultimate clinical applicability. From this data, 39 antigens were selected based on sensitivity by visual and/or statistical analysis. Statistically, they had to meet two of the following criteria for selection, >10% sensitivity at 95% specificity, AUC ≥0.44, and a K-statistic ≥0.9.

RAPID ELISA Test of 39 Antigen Biomarkers Associated with Serous Ovarian Cancer

We performed an orthogonal RAPID ELISA assay to validate our 39 candidate TAAb biomarkers. The RAPID ELISA assay is highly reproducible and readily amenable for screening large numbers of sera [16]. First, we rescreened the 39 antigens against our training set serum samples in order to establish cutoff values, sensitivity, and specificity for each antigen in comparison to benign disease and healthy controls. All 39 antigens were assessed using cutoff values defined by the benign disease control samples. In the training set screen, antibodies against NUDT11 (27.5%), TRIM39 (24.1%), KSR1 (13.7%), and PVR (13.7%) demonstrated the best discrimination of serous ovarian cancer from benign disease controls at 93.3% and 96.7% specificity (Table 2). We selected a panel of the top 11 antigens (CTAG2, ICAM3, KSR1, NUDT11, NXF3, POMC, PVR, STYXL1, p53, TRIM39, and UHMK1) based on their sensitivity (3.4 to 27.5%) and specificity (90 to 100%). Using this panel, we calculated the overall sensitivity and specificity of training set, defining a patient as positive if they express ≥2 antigens. The combined overall sensitivity of the top 11 antigens for discriminating benign disease (37.9%) and healthy (31%) controls at 93% specificity, are presented in Table 2. In addition, all of the cases and benign disease controls were screened for CA125 prior to treatment. There were 5 cases that were falsely negative (below 35 U/mL) for CA125. Using our final panel of 11-AAb, all 5 cases were classified as positive. Similarly, there were 6 benign disease controls with false positive CA125 values (above 35 U/mL) and using our 11-AAb panel the specificity of CA125 improved to 2 false positives.

Validation of Biomarkers and Development of the 11 Autoantibody Panel

Figure 3A:
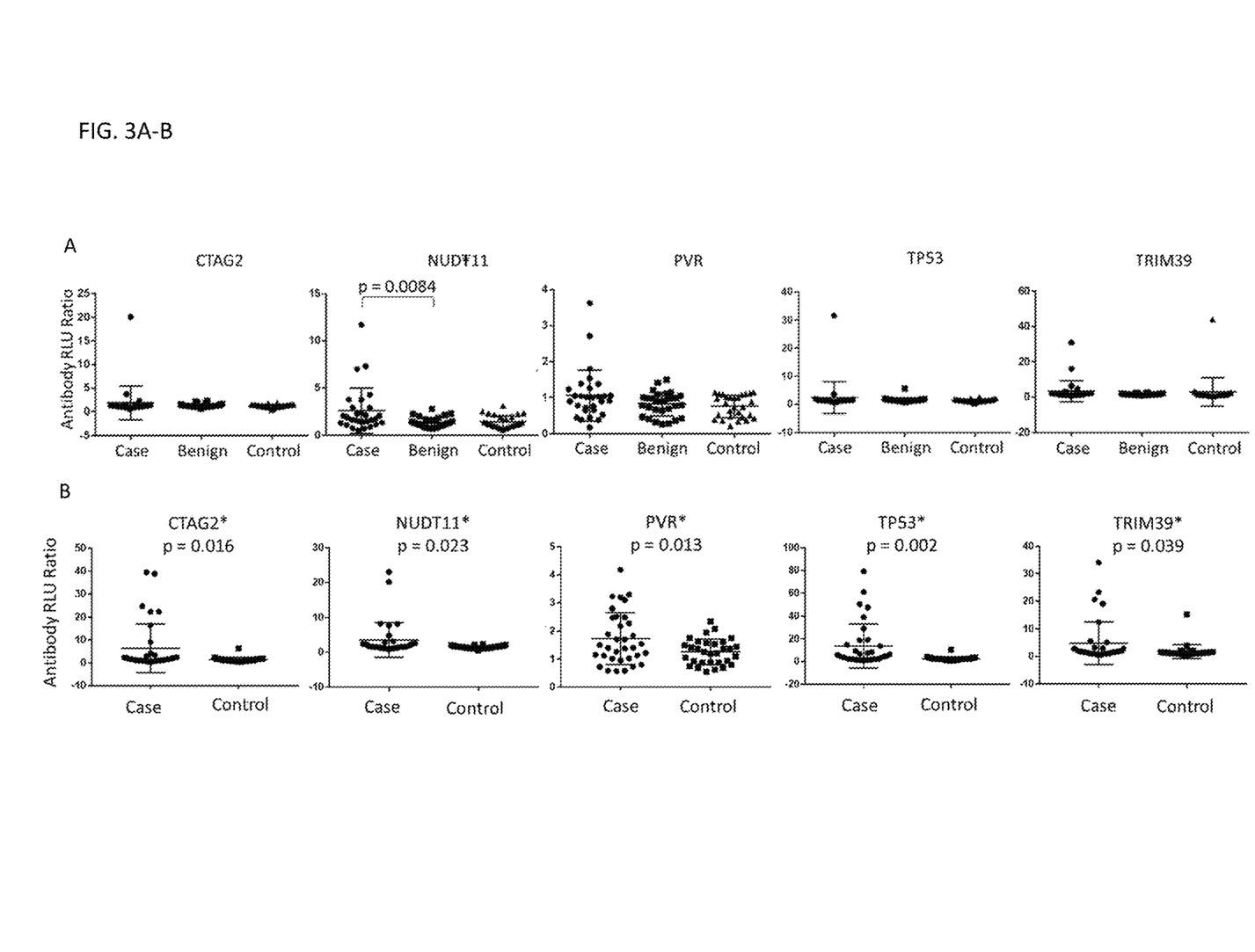

We screened the top 11 antigens against an independent validation 2 sera set consisting of 34 cases of serous ovarian cancer and 32 healthy controls (FIGS. 1 and 3, Table 2). In validation set, TAAb against p53, CTAG2, NUDT11, PVR, and ICAM3 had sensitivities ≥17.6% at specificities of ≥96.8%; with a combined sensitivity of 47.1% at 93.7% specificity using the same criteria as our training set (Table 2).

Figure 4A:
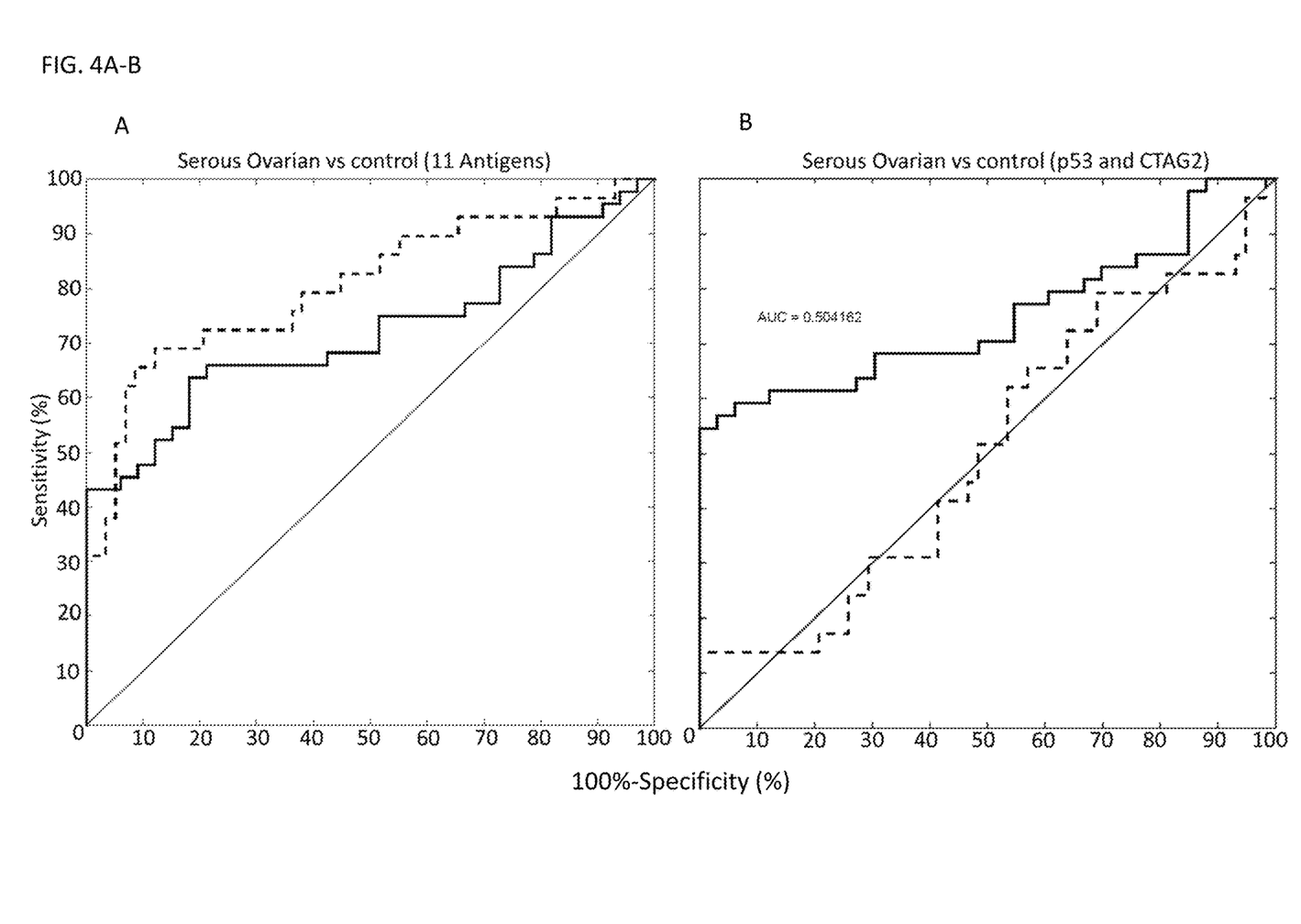

A receiver operating characteristic (ROC) analysis was computed using a binary logistic regression analysis (see Material and Methods). The 11 TAAb classifier was trained using antibody relative light unit (RLU) ratios from our training set comparing serous ovarian cases against benign disease and healthy controls with an area under the curve (AUC) of 0.807 and a sensitivity of 32% at 100% specificity (FIG. 4A, dotted line, Supplemental Table 4). We tested our classifier using antibody RLU ratios from our validation set comparing serous ovarian cases against healthy controls with an ROC of 0.719 at a sensitivity of 45% at >99% specificity (FIG. 4A, solid line). In comparison, we generated a separate classifier utilizing the same training and test samples for the top two TAAb to serous ovarian cancer, p53 and CTAG2 (FIG. 4B). While this could be due to the unexpected improvement in sensitivity from the training set to the validation set; this suggests that p53 and CTAG2 alone have a higher sensitivity and AUC when discriminating serous ovarian cases from healthy controls but on their own do not discriminate serous ovarian cases from benign disease controls. In addition, all cases were screened for CA125 prior to treatment. In our validation sample set there were 5 cases that were false negative for CA125. Using our 11-AAb panel, four of the five false negative CA125 cases were classified as positive, improving the sensitivity of the CA125 assay.

Discussion

Sera samples from a total of 94 patients with serous ovarian cancer and 30 benign disease and 92 healthy control samples were screened for TAAb using our custom protein microarrays (Discovery and Training Sets). We identified an 11-AAb biomarker panel that distinguishes serous ovarian cancer from benign disease (32% sensitivity) and healthy controls (45% sensitivity) at 98% specificity (FIG. 4A). Five of these markers have been previously identified in serous ovarian cancer (p53 and CTAG2) or related cancers (NUDT11, PVR, and TRIM39) as contributing to cancer progression. Three biomarkers, NUDT11, PVR, and TRIM39 were consistently selective for serous ovarian cancer with individual sensitivities ranging from 14.7% to 32.4% at >96% specificity. Previously identified biomarkers for serous ovarian cancer, p53 and CTAG2 displayed modest sensitivities 6.9% and 10.3% at 98% specificity discriminating serous ovarian cancer from benign disease controls but displayed higher sensitivities 44.1% and 23.5% at >96% specificity when compared to healthy controls.

Previous work on serous ovarian cancer associated TAAbs have focused on the detection of individual biomarkers with only recent attention being given to the development of a panel of TAAb [4]. Ovarian cancer is usually detected at late stages and with high mortality rates. CA 125 (MUC19) is a glycoprotein biomarker that detects 50% of early stage ovarian cancer and remains, to this day, the primary biomarker for ovarian cancer diagnosis in routine clinical use [3]. HE4 shows similar diagnostic properties as CA 125 [26]. Other potential biomarkers include MMP1 [27], cytokines [28], plasminogen activator receptor [29], osteopontin [9], MMP7 [30], B7-H4 [31], and kallikreins [32]. The use of multiple tumor markers may improve the performance characteristics of the tests [26]. In a phase III blinded validation study only serum concentrations of CA 125, HE4, and mesothelin have been shown to increase up to 3 years prior to clinical diagnosis [33]. This multimodal screening (MMS) strategy is further highlighted in the recent report from the UK Collaborative Trial of Ovarian Cancer Screening (UKCTOCS), in which more than 200,000 women were followed for 14 year to assess the effects of early/annual screening on ovarian cancer mortality rates [34]. The finding, overall, suggests that annual long-term MMS reduces mortality rates by up to 28% compared to no screening. These two studies emphasize the importance of annual screening using a panel of biomarkers, multiple screening approaches, and detailed screening algorithms to reduce the mortality rates associated with ovarian cancer.

In our prior study using first generation NAPPA arrays we identified a panel of 12 TAAb with sensitivities ranging from 13% to 22% at >93% specificity [16]. Epitope presentation is critical for serological assays and it has been recently reported that over 90% of antibodies are generated against conformational epitopes, stressing the importance of protein folding and post-translational modifications for the identification of TAAb biomarkers [35]. Our first generation NAPPA arrays used rabbit reticulocyte lysate to perform IVTT [16]. Rabbit reticulocyte is a mammalian IVTT expression system with several drawbacks, including limited post-translation modifications and co-expression of off-target proteins, thus leading to high-background, batch-to-batch variability, and suboptimal expression conditions. In this study, we used improved second generation NAPPA arrays displaying >5,000 new full-length proteins as well as mammalian Hela cell lysate to express optimized and normalized cDNAs, providing higher protein yields. These changes have improved our reproducibility, lowered background, and increased assay sensitivity.

In addition to p53, we consistently identified TAAb to the previously reported CTAG2, as well as three novel ovarian autoantigens PVR, NUDT11, and TRIM39. While PVR was present on our first generation arrays both NUDT11 and TRIM39 are recent additions to our second generation arrays. We reconfirmed the presence of TAAbs to (p53, CTAG, and PVR) in serous ovarian cancer [16]. Tumor antigen-associated autoantibodies against p53 and CTAG2 proteins have been reported by our group as well as others as biomarkers for several tumor types such as serous ovarian [16], basal-like breast [11], and lung cancer [17]. Interestingly, TAAb against p53 and CTAG2 correlate with aggressive phenotypes of these cancers. The similar transcript expression profiles of ovarian, basal-like and lung cancer reported by The Cancer Genome Atlas (TCGA) suggest that these markers may have value in detecting multiple cancers [36].

Of the novel biomarkers we identified, several are associated with carcinogenesis. The family of nudix (NUDT) proteins, including NUDT11, are highly conserved among species and contribute to the hydrolysis of nucleoside diphosphate derivatives, hypothesized to control the cellular concentration of these compounds [37]. While the role of NUDT11 is unknown, there are studies supporting the role of NUDT1 driving cellular proliferation in breast, lung, colon, and prostate cancer [38]. Poliovirus receptor (PVR, also known as CD155) is an overexpressed cell surface protein in multiple tumor types that contributes to proliferation, invasion, and immune evasion [39]. PVR/CD155 has been the recent target of oncolytic viral therapies, due to the abundant overexpression on tumor cells [40]. The TRIM family of proteins display both a positive and negative role in regulating oncogenesis by ubiquitinating key regulatory proteins such as p53 [41]. Although TRIM39 has not been directly implicated in tumor progression recent studies have demonstrated that TRIM39 can directly bind to and ubiquitinate p53, stabilizing p21 and leading to cell cycle progression in hepatocellular carcinoma [42].

There are several limitations of this study. First, there is evident variation in the frequency of TAAb detection between our training set and validation sets. We suspect that this may be due to the significantly older population in the validation set, which did not include benign disease controls (Table 1). These results warrant further evaluation with independent samples sets. We do not yet know how early these biomarkers are detected prior to ovarian cancer development, but p53-AAb have been detected up to 6 months prior to clinical disease [16, 18].

In summary, we performed the largest proteomic screen using programmable protein arrays to date on serous ovarian cancer and identified an 11-TAAb biomarker panel. Further validation of these markers is needed using independent sample sets. Early ovarian cancer diagnosis is limited by both the overall low incidence of the disease in the general population (1.5% lifetime risk) and the rapid development of peritoneal disease [4]. Routine screening with CA 125 serum levels, transvaginal ultrasound, and pelvic examinations has not been shown to improve morbidity or mortality from ovarian cancer [1]. Our analysis of TAAb associated with serous ovarian cancer represents promising markers for the early detection because their sensitivity is independent of TVUS, and blood tests can be performed often to determine the longitudinal changes in biomarker levels of high risk individuals without risk or expensive tests, providing a realistic approach for individuals who require more frequent testing. Early evaluation of these markers complement CA 125, improving sensitivity as well as improving the specificity of CA 125 for the evaluation of benign ovarian disease. Future work is needed to determine if these markers provide clinical value for diagnostic and/or prognostic responses.

REFERENCES

[1] Society AC. Cancer Facts & Figures 2015. Atlanta: American Cancer Society. 2015.

[2] Fast Stats: An interactive tool for access to SEER cancer statistics. Surveillance Research Program NCIhscgf.

[3] Badgwell D, Bast R C, Jr. Early detection of ovarian cancer. Dis Markers. 2007; 23:397-410.

[4] Shi J X, Qin J J, Ye H, Wang P, Wang K J, Zhang J Y. Tumor associated antigens or anti-TAA autoantibodies as biomarkers in the diagnosis of ovarian cancer: a systematic review with meta-analysis. Expert review of molecular diagnostics. 2015; 15:829-52.

[5] Jacobs I J, Menon U, Ryan A, Gentry-Maharaj A, Burnell M, Kalsi J K, et al. Ovarian cancer screening and mortality in the UK Collaborative Trial of Ovarian Cancer Screening (UKCTOCS): a randomised controlled trial. Lancet. 2015.

[6] Anderson K S, LaBaer J. The sentinel within: exploiting the immune system for cancer biomarkers. Journal of proteome research. 2005; 4:1123-33.

[7] Koziol J A, Zhang J Y, Casiano C A, Peng X X, Shi F D, Feng A C, et al. Recursive partitioning as an approach to selection of immune markers for tumor diagnosis. Clin Cancer Res. 2003; 9:5120-6.

[8] Chapman C, Murray A, Chakrabarti J, Thorpe A, Woolston C, Sahin U, et al. Autoantibodies in breast cancer: their use as an aid to early diagnosis. Ann Oncol. 2007; 18:868-73.

[9] Chatterjee M, Mohapatra S, Ionan A, Bawa G, Ali-Fehmi R, Wang X, et al. Diagnostic markers of ovarian cancer by high-throughput antigen cloning and detection on arrays. Cancer Res. 2006; 66:1181-90.

[10] Anderson K S, Sibani S, Wong J, Hainsworth G, Mendoza E A, Eugene R, Raphael J, Logvinenko T, Ramachandran N, Godwin A, Marks J, Engstrom P, and LaBaer J. Using custom protein microarrays to identify autoantibody biomarkers for the early detection of breast cancer. San Antonio Breast Cancer Symposium. San Antonio, TX2008.

[11] Wang J, Figueroa J D, Wallstrom G, Barker K, Park J G, Demirkan G, et al. Plasma Autoantibodies Associated with Basal-like Breast Cancers. Cancer Epidemiol Biomarkers Prev. 2015; 24:1332-40.

[12] Katchman B A, Barderas R, Alam R, Chowell D, Field M S, Esserman L J, et al. Proteomic Mapping of p53 Immunogenicity in Pancreatic, Ovarian, and Breast Cancers. Proteomics Clin Appl. 2016.

[13] Wang X, Yu J, Sreekumar A, Varambally S, Shen R, Giacherio D, et al. Autoantibody signatures in prostate cancer. N Engl J Med. 2005; 353:1224-35.

[14] Pedersen J W, Gentry-Maharaj A, Fourkala E O, Dawnay A, Burnell M, Zaikin A, et al. Early detection of cancer in the general population: a blinded case-control study of p53 autoantibodies in colorectal cancer. British journal of cancer. 2013; 108:107-14.

[15] Lubin R, Zalcman G, Bouchet L, Tredanel J, Legros Y, Cazals D, et al. Serum p53 antibodies as early markers of lung cancer. Nature medicine. 1995; 1:701-2.

[16] Anderson K S, Cramer D W, Sibani S, Wallstrom G, Wong J, Park J, et al. Autoantibody signature for the serologic detection of ovarian cancer. Journal of proteome research. 2015; 14:578-86.

[17] Desmetz C, Mange A, Maudelonde T, Solassol J. Autoantibody signatures: progress and perspectives for early cancer detection. J Cell Mol Med. 2011; 15:2013-24.

[18] Anderson K S, Wong J, Vitonis A, Crum C P, Sluss P M, Labaer J, et al. p53 autoantibodies as potential detection and prognostic biomarkers in serous ovarian cancer. Cancer Epidemiol Biomarkers Prev. 2010; 19:859-68.

[19] Anderson K S, Ramachandran N, Wong J, Raphael J V, Hainsworth E, Demirkan G, et al. Application of protein microarrays for multiplexed detection of antibodies to tumor antigens in breast cancer. Journal of proteome research. 2008; 7:1490-9.

[20] Anderson K S. Multiplexed detection of antibodies using programmable bead arrays. Methods in molecular biology. 2011; 723:227-38.

[21] Ramachandran N, Raphael J V, Hainsworth E, Demirkan G, Fuentes M G, Rolfs A, et al. Next-generation high-density self-assembling functional protein arrays. Nature methods. 2008; 5:535-8.

[22] Vitonis A F, Titus-Ernstoff L, Cramer D W. Assessing ovarian cancer risk when considering elective oophorectomy at the time of hysterectomy. Obstet Gynecol. 2011; 117:1042-50.

[23] Cramer D W, Vitonis A F, Welch W R, Terry K L, Goodman A, Rueda B R, et al. Correlates of the preoperative level of CA125 at presentation of ovarian cancer. Gynecol Oncol. 2010; 119:462-8.

[24] Wang J, Barker K, Steel J, Park J, Saul J, Festa F, et al. A versatile protein microarray platform enabling antibody profiling against denatured proteins. Proteomics Clin Appl. 2013; 7:378-83.

[25] Wong J, Sibani S, Lokko N N, LaBaer J, Anderson K S. Rapid detection of antibodies in sera using multiplexed self-assembling bead arrays. Journal of immunological methods. 2009; 350:171-82.

[26] Moore R G, McMeekin D S, Brown A K, DiSilvestro P, Miller M C, Allard W J, et al. A novel multiple marker bioassay utilizing HE4 and CA125 for the prediction of ovarian cancer in patients with a pelvic mass. Gynecol Oncol. 2009; 112:40-6.

[27] Bertenshaw G P, Yip P, Seshaiah P, Zhao J, Chen T H, Wiggins W S, et al. Multianalyte profiling of serum antigens and autoimmune and infectious disease molecules to identify biomarkers dysregulated in epithelial ovarian cancer. Cancer Epidemiol Biomarkers Prev. 2008; 17:2872-81.

[28] Zhang Z, Yu Y, Xu F, Berchuck A, van Haaften-Day C, Havrilesky L J, et al. Combining multiple serum tumor markers improves detection of stage I epithelial ovarian cancer. Gynecol Oncol. 2007; 107:526-31.

[29] Henic E, Borgfeldt C, Christensen I J, Casslen B, Hoyer-Hansen G. Cleaved forms of the urokinase plasminogen activator receptor in plasma have diagnostic potential and predict postoperative survival in patients with ovarian cancer. Clin Cancer Res. 2008; 14:5785-93.

[30] Palmer C, Duan X, Hawley S, Scholler N, Thorpe J D, Sahota R A, et al. Systematic evaluation of candidate blood markers for detecting ovarian cancer. PLoS ONE. 2008; 3:e2633.

[31] Simon I, Liu Y, Krall K L, Urban N, Wolfert R L, Kim N W, et al. Evaluation of the novel serum markers B7-H4, Spondin 2, and DcR3 for diagnosis and early detection of ovarian cancer. Gynecol Oncol. 2007; 106:112-8.

[32] Yousef G M, Diamandis E P. The human kallikrein gene family: new biomarkers for ovarian cancer. Cancer Treat Res. 2009; 149:165-87.

[33] Anderson G L, McIntosh M, Wu L, Barnett M, Goodman G, Thorpe J D, et al. Assessing lead time of selected ovarian cancer biomarkers: a nested case-control study. J Natl Cancer Inst.102:26-38.

[34] Jacobs I J, Menon U, Ryan A, Gentry-Maharaj A, Burnell M, Kalsi J K, et al. Ovarian cancer screening and mortality in the UK Collaborative Trial of Ovarian Cancer Screening (UKCTOCS): a randomised controlled trial. Lancet. 2016; 387:945-56.

[35] Murphy M A, O'Connell D J, O'Kane S L, O'Brien J K, O'Toole S, Martin C, et al. Epitope presentation is an important determinant of the utility of antigens identified from protein arrays in the development of autoantibody diagnostic assays. Journal of proteomics. 2012; 75:4668-75.

[36] Reuschenbach M, von Knebel Doeberitz M, Wentzensen N. A systematic review of humoral immune responses against tumor antigens. Cancer immunology, immunotherapy: CII. 2009; 58:1535-44.

[37] Nakabeppu Y. Cellular levels of 8-oxoguanine in either DNA or the nucleotide pool play pivotal roles in carcinogenesis and survival of cancer cells. International journal of molecular sciences. 2014; 15:12543-57.

[38] Grisanzio C, Werner L, Takeda D, Awoyemi B C, Pomerantz M M, Yamada H, et al. Genetic and functional analyses implicate the NUDT11, HNF1B, and SLC22A3 genes in prostate cancer pathogenesis. Proceedings of the National Academy of Sciences of the United States of America. 2012; 109:11252-7.

[39] Kono T, Imai Y, Yasuda S, Ohmori K, Fukui H, Ichikawa K, et al. The CD155/poliovirus receptor enhances the proliferation of ras-mutated cells. International journal of cancer Journal international du cancer. 2008; 122:317-24.

[40] Brown M C, Dobrikova E Y, Dobrikov M I, Walton R W, Gemberling S L, Nair S K, et al. Oncolytic polio virotherapy of cancer. Cancer. 2014; 120:3277-86.

[41] Hatakeyama S. TRIM proteins and cancer. Nature reviews Cancer. 2011; 11:792-804.

[42] Zhang L, Mei Y, Fu N Y, Guan L, Xie W, Liu H H, et al. TRIM39 regulates cell cycle progression and DNA damage responses via stabilizing p21. Proceedings of the National Academy of Sciences of the United States of America. 2012; 109:20937-42.

The claims are not meant to be limited to the materials and methods, embodiments, and examples described herein.

We claim:

1. A method comprising the steps of:
    contacting a fluid from a patient that contains a tumor antigen-associated autoantibody (TAAb) with a panel of antigens, thereby forming an antigen/TAAb complex in vitro if said TAAb binds an antigen on said panel, wherein said panel of antigens consists of cancer/testis antigen 2 (CTAG2), cellular tumor antigen p53 (p53), poliovirus receptor (PVR), diphosphoinositol polyphosphate phosphohydrolase 3-beta (NUDT11), intercellular adhesion molecule 3 (ICAM3), E3 ubiquitin-protein ligase TRIM39 (TRIM39), serine/threonine/tyrosine-interacting-like protein 1 (STYXL1), Pro-opiomelanocortin (POMC), serine/threonine-protein kinase Kist (UHMK1), kinase suppressor of Ras 1 (KSR1), and nuclear RNA export factor 3 (NXF3), wherein antigens in the panel are linked to a solid support; and
    detecting whether each antigen in the panel of antigens forms an antigen/TAAb complex.

2. The method of claim 1, wherein said panel of antigens comprises a Nucleic Acid Protein Programmable Array (NAPPA).

3. A method for administering a diagnostic procedure or a therapeutically effective treatment following early stage ovarian cancer detection in a patient, comprising the steps of:
    (a) contacting a fluid that contains immunoglobulins from said patient with a substrate comprising biomarkers, wherein the substrate comprises a solid support, the biomarkers consisting of ICAM3, CTAG2, p53, STYXL1, PVR, POMC, NUDT11, TRIM39, UHMK1, KSR1, and NXF3;
    (b) detecting whether each biomarker is bound by the patient's immunoglobulins; and
    (c) administering a diagnostic procedure or a therapeutically effective treatment based on the detecting in step (b).

4. The method of claim 3, further comprising administering a therapeutically effective treatment for said patient, the treatment selected from the group consisting of a surgical intervention, a chemotherapeutic intervention, and a radiotherapeutic intervention, if two or more biomarkers are detected.

5. The method of claim 1, wherein said solid support comprises a 96-well plate.

6. The method of claim 3, wherein the solid support comprises a 96-well plate.

7. The method of claim 3, wherein the substrate comprising biomarkers comprises a Nucleic Acid Protein Programmable Array (NAPPA).

* * * * *